United States Patent [19]

Milligan et al.

[11] 4,257,986
[45] Mar. 24, 1981

[54] PROCESS FOR REFINING AQUEOUS ACID MIXTURES UTILIZED IN NITRATION OF AROMATICS

[75] Inventors: Barton Milligan, Coplay, Pa.; Der-Shing Huang, Carmichael, Calif.

[73] Assignee: Air Products and Chemicals, Inc., Allentown, Pa.

[21] Appl. No.: 8,906

[22] Filed: Feb. 2, 1979

[51] Int. Cl.³ .............................................. C07C 79/10
[52] U.S. Cl. .................................. 568/934; 423/523; 423/531
[58] Field of Search ................. 260/645; 423/523, 531

[56] References Cited

U.S. PATENT DOCUMENTS

| | | | |
|---|---|---|---|
| 2,355,702 | 8/1944 | Brooks | 423/531 |
| 2,773,911 | 12/1956 | Dubois et al. | 260/645 |
| 2,849,497 | 8/1958 | Buchanan | 260/645 |
| 2,971,819 | 2/1961 | Antelman | 423/531 |
| 3,204,000 | 8/1965 | Samuelsen | 260/645 |
| 3,856,673 | 12/1974 | La Mater | 423/531 |
| 4,155,989 | 5/1979 | Miller | 423/531 |

FOREIGN PATENT DOCUMENTS 1061753  7/1959  Fed. Rep. of Germany ........... 423/531

OTHER PUBLICATIONS

"Removal of Nitrose from Sulfuric Acid", Chem. Abstracts, vol. 53 (1959) Abstract #8557d.

*Primary Examiner*—Deborah L. Kyle
*Attorney, Agent, or Firm*—E. Eugene Innis; Russell L. Brewer

[57] ABSTRACT

This invention relates to an improvement in a process for the manufacture of a nitroaromatic compound produced by the mixed sulfuric-nitric acid nitration method. The improvement resides in the refining of the aqueous acid mixture and comprises the following sequential steps: (a) contacting the mixed aqueous acid mixture, after nitration, with an oxidizing or a reducing agent under conditions effective for removing contaminant nitrous acid; (b) contacting the aqueous acid mixture in step (a) with feed aromatic compound to remove contaminant organics and residual nitric acid and then, if necessary, (c) contacting the remaining acid mixture with sufficient oxidizing agent under oxidizing conditions to remove residual organic components.

8 Claims, 1 Drawing Figure

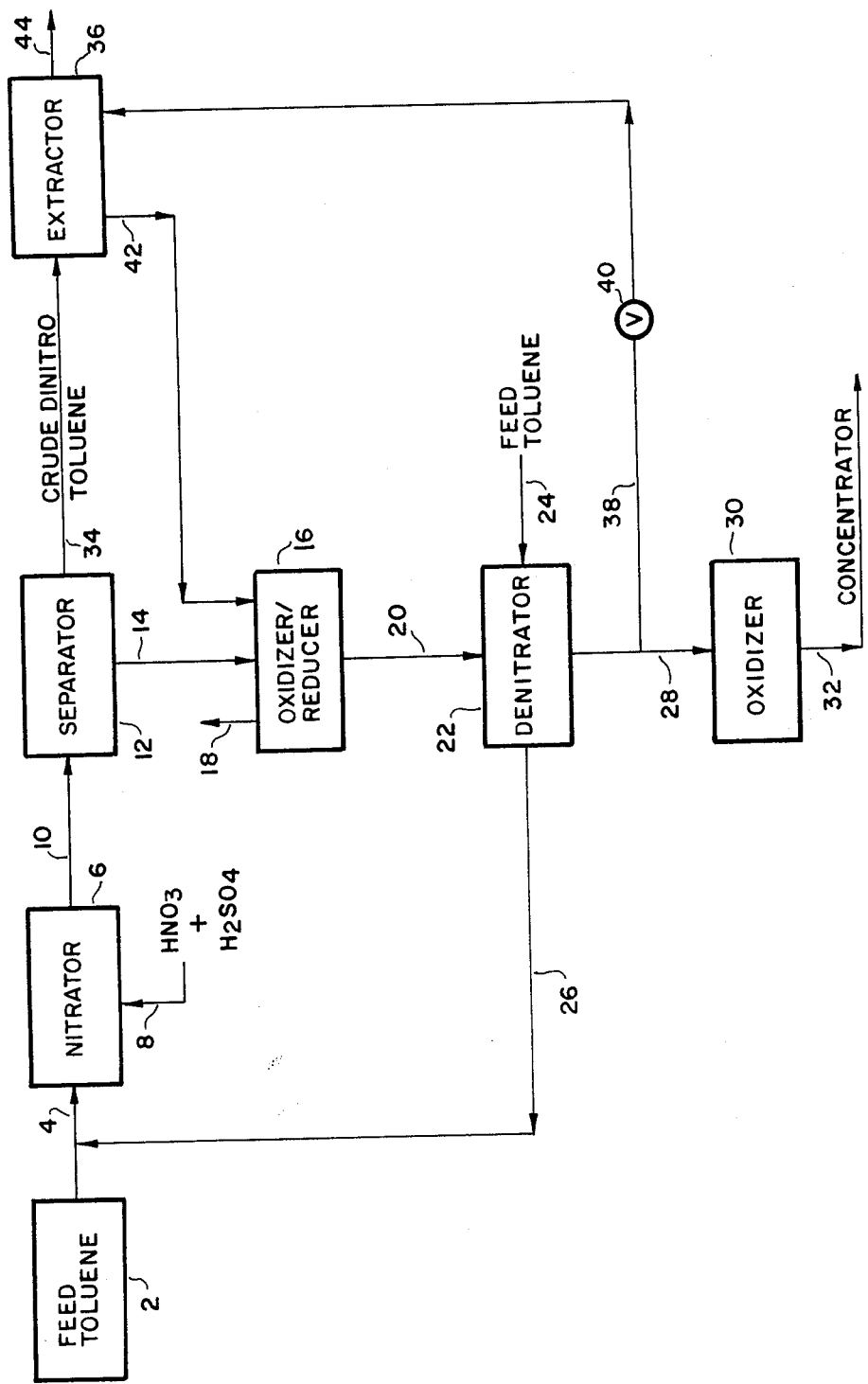

PROCESS FOR REFINING AQUEOUS ACID MIXTURES UTILIZED IN NITRATION OF AROMATICS

BACKGROUND OF THE INVENTION

1. Field of the Invention

This invention relates to a process for refining the aqueous acid mixture obtained from the mixed acid nitration of aromatic compounds. More particularly, it is directed to a process for refining the sulfuric acid utilized in the nitration reaction so that the end product will be substantially free of contaminant material and color.

2. Description of the Prior Art

U.S. Pat. No. 3,856,673 relates to a process for refining sulfuric acid utilized in the mixed acid nitration of aromatic compounds, e.g. benzene and toluene. As disclosed in the prior art section, it was common practice to steam strip the spent acid mixture obtained from the nitrator to remove volatile organic and inorganic impurities e.g. nitrous acid, sulfur compounds, and nitrous oxides. It was pointed out that the nonvolatile organic compounds remained in the sulfuric acid and had to be bled from the system or as disclosed in the patent, oxidized with an oxidizing agent to volatile products.

U.S. Pat. No. 3,204,000 discloses a process for producing nitrotoluene in a continuous nitration process. The pertinent portion of this patent lies in its disclosure of the purification technique for the aqueous acid mixture. The patentee points out in column 1, lines 50-60 that substantial quantities of deleterious nitrous acid are produced during nitration particularly when the dinitrotoluene concentration is high. At column 2, lines 5-20, it is pointed out that nitrous acid can be removed by increasing the nitric acid concentration but that undesired side reactions resulting in a discolored nitrotoluene product and acid attack of the stainless steel reactor results. Another technique utilized for removing nitrous acid involved passing air through a separator and stripping with dilute nitric acid.

U.S. Pat. No. 2,849,497 discloses a process for producing nitrobenzene with particular emphasis on refining the crude nitrobenzene produced. In that patent, the aqueous acid mixture obtained from the nitrator is separated from crude nitrobenzene in a settling tank. The spent acid is passed to a denitrator where it is contacted with feed benzene to form a crude benzene-nitrobenzene product which is then passed to the nitrator. A portion of the sulfuric acid product from the denitrator then is contacted with the crude nitrobenzene for the purpose of scrubbing residual nitric acid dissolved therein and then it is returned to the denitrator. Another portion of the sulfuric acid from the denitrator is sent to a sulfuric acid concentrator where it is reconstituted for reuse.

SUMMARY OF THE INVENTION

This invention relates to a process for the refining of an agueous sulfuric-nitric acid mixture utilized in the nitration of an aromatic hydrocarbon. The refining technique involves the following steps:

(a) contacting the aqueous acid mixture obtained from the reaction of an aromatic compound with aqueous nitric acid in the presence of sulfuric acid with an agent under conditions effective for removing contaminant nitrous acid contained therein;

(b) contacting the aqueous acid mixture free of nitrous acid obtained in step (a) with a sufficient quantity of feed aromatic compound to remove residual nitric acid therefrom leaving a product consisting essentially of sulfuric acid and contaminant organic impurities; and then (c) if necessary, contacting the acid mixture with an oxidizing agent under conditions sufficient to remove and oxidize the residual organic impurities in the acid mixture.

There are several advantages associated with the process of this invention and these advantages include:

an ability to produce a clean product with simple equipment thus minimizing maintenance problems associated with prior art techniques e.g. steam stripping;

an ability to remove dissolved product dinitrotoluene and other organics from the sulfuric acid thus providing for an enhanced recovery of product and a mechanism for producing clean sulfuric acid;

an ability to produce sulfuric acid which can either be reused in the nitration process or for commercial use, the acid being free of undesirable color bodies;

an ability to recover substantially all of the unreacted nitric acid by converting it to nitrated product; and an ability to refine the aqueous acid mixture by elimination of high energy consuming steam stripping techniques.

IN THE DRAWING

The drawing is a block flow diagram of a dinitrotoluene plant utilizing the refining technique of this invention.

DESCRIPTION OF THE PREFERRED EMBODIMENT

Referring to the drawing, feed toluene obtained from storage tank 2, is conveyed by way of line 4 to nitrator 6 where it is converted into mononitro and dinitrotoluene by the conventional mixed acid technique. Although toluene is used in this process, other aromatic compounds such as benzene, xylene and chlorotoluene could be substituted for toluene and nitrated in conventional manner. Nitration typically is effected by first charging aqueous, nitric and sulfuric acid through line 8 to nitrator 6, the concentration of mixed acid being about 60 to 85% sulfuric acid, 10, to 30% nitric acid, and 3 to 16% water and then charging the toluene and reacting at conventional temperatures and pressures. After the nitration is complete, the curde nitrotoluene product, including the aqueous acid mixture, is removed through line 10 where it is passed to gravity separator 12. In gravity separator 12 the organic phase is separated from the heavier aqueous acid phase.

The refining technique for the mixed acid is carried out in the following manner. The aqueous acid mixture as it obtained from separator 12 is passed through line 14 and charged to oxidizer or reducer tank 16. The aqueous acid mixture, particularly where a large concentration of dinitrotoluene is produced, will contain substantial quantities, e.g. greater than 100 ppm of nitrous acid and other impurities. In the case where benzene is utilized as the reactant and mononitrobenzene is the product, the quantities of nitrous acid will be smaller. However, unless the acid is stripped periodically the nitrous acid will build up to a higher concentration and cause problems.

The aqueous acid mixture in tank 16 is contacted with a conventional oxidizing agent which is effective for destroying nitrous acid and converting it to nitric acid or with a conventional reducing agent which converts it to innocuous nitrogen or nitric oxide. Vapors can be removed overhead in line 18 vapors. As indicated, either an oxidizing agent or a reducing agent may be used to convert the nitrous oxide to an innocuous material. The selection generally is based primarily on cost and conversion time. Specific examples of oxidizing agents suited for destroying nitrous acid include hydrogen peroxide, sodium and potassium peroxydisulfates, sodium and potassium chlorates and chlorites. Specific examples of reducing agents include sulfamic acid, urea, ammonium sulfate, and formamide.

The oxidizing or reducing agent is utilized in at least stoichiometric quantites based on the level of nitrous acid in the aqueous acid mixture, and preferably in excess up to about 1.6 moles per mole of nitrous acid. Higher quantites can be utilized in the step although no significant procedural advantages are achieved. In the case where an oxidizing agent is used, concentrations above stoichiometric tend to impart color. Conditions effective for converting nitrous acid to innocuous vapors or nitric acid generally involve a reaction temperature of about 20° to 60° C. and a contact time of about 1-30 minutes. Such oxidation or reducing conditions are known in the art.

Treatment of the spent acid with an oxidizing or reducing agent was found to be necessary if one wanted to elminiate color bodies in the spent sulfuric acid. Toluene extraction prior to oxidation left a highly colored reddish acid product. After experimentation and testing we believe the color is caused by a product resulting from the reaction of $HNO_2$ with the aromatic feed. Experimental evidence shows that when the $HNO_2$ content is less than about 10 ppm, preferably 1 ppm, very little to no discoloration of the sulfuric acid is observed. When the level of $HNO_2$ exceeds about 25 ppm color bodies appear.

The aqueous acid mixture free of nitrous acid is removed from tank 16 through line 20 and charged to denitrator 22. In denitrator 22 sufficient feed aromatic compound, e.g. toluene, is intimately mixed with the aqueous acid mixture so that substantially all of the residual nitric acid in the mixture is removed. In the scrubbing operation feed aromatic compound is reacted with $HNO_3$ to produce a crude nitrated product. The scrubbing of the aqueous acid mixture in denitrator 22 generally is conducted at a temperature of about 10° to 50° C. for a time about 1 to 60 minutes in order to effect reaction of the nitric acid with the feed. The quantity of feed aromatic compound passed through denitrator 22 must be at least a stoichiometric quantity based on the nitric acid concentration. Other factors which affect the quantity of aromatic feed as extractent are: there should be sufficient feed to permit easy separation from the aqueous phase and there should not be substantial excess over the feed requirements. Higher concentrations of feed add insignificant benefit. Generally, the quantity of aromatic used for extraction is from 10-100% of the total feed aromatic used in the process and preferably 20-40% (volume basis). The crude product after effecting removal of the nitric acid is removed via line 26 and combined with the feed toluene in line 4 for nitration.

Although the process, as disclosed, shows separate steps for the removal of nitrous acid and the denitration of the aqueous acid mixture via the introduction of feed toluene, these steps can be combined and carried out substantially simultaneously. To carry out the process substantially simultaneously, a small amount of oxidizer or reducer is incorporated into denitrator 22. In a preferred case, it is preferred to keep the steps separate.

The aqueous sulfuric acid mixture, free of nitrous acid and nitric acid, is removed from denitrator 22 via line 28. The stream typically contains organic impurities, e.g. at a level greater than 100 ppm which should be removed prior to concentrating or reusing the acid in other processes. If contaminant organic removal is desired, the stream is sent to a second oxidizing tank for removal of the residual organic material. The conditions necessary for effecting decomposition of the organic contaminants in the aqueous acid mixture are essentially those set forth in U.S. Pat. No. 3,856,673, and such conditions are incorporated by reference. Oxidizing agents suited for removing the organic components are ozone, hydrogen peroxide, peroxydisulfates, such as sodium and potassium peroxydisulfate and chlorates and chlorites such as sodium and potassium chlorates and sodium and potassium chlorites. The temperatures utilized in oxidizer 30 generally will vary from about 130°-230° C., and the reaction time should be for about 1 to 60 minutes. The concentration of organic component in the acid mixture as it is withdrawn from oxidizer 30 via line 32, should be less than about 50 parts per million (ppm). The final product obtained from line 32 will consist essentially of aqueous sulfuric acid with a concentration of about 60 to 75% by weight. This acid then can be concentrated for reuse in the nitration system or can be sold in dilute form for commercial utilization.

An optional refinement in the overall process resides in the scrubbing of the crude nitroaromatic composition e.g. crude dinitrotoluene obtained from separator 12. More specifically, the crude dinitrotoluene from separator 12 is conveyed by line 34 to extractor 36. There a sidestream of denitrated acid is conveyed by line 38 with the amount being regulated by control valve 40. The denitrated acid is intimately contacted with the crude dinitrotoluene to remove substantially all of the residual nitric acid dissolved in the dinitrotoluene. The aqueous mixture then is removed from extractor 36 via line 42 and sent to tank 16 for reprocessing. The scrubbed dinitrotoluene product iss removed from extractor 36 by line 44 and processed in conventional manner.

Another optional feature, but not shown, resides in the recovery of feed toluene prior to oxidation in tank 30. The toluene can be removed by air sparging or solvent extraction. In the latter case butane is used to scrub residual toluene from the acid, the butane being separated from the toluene by distillation.

The following examples are provided to illustrate a preferred method for practicing the invention and is not intended to limit the scope thereof as other alternative ways are available.

EXAMPLE 1: Prior Art

A spent acid obtained from the dinitration of toluene was used as a feed material for refinement. The components and concentration in the spent acid feed was as follows:

| | |
|---|---|
| Sulfuric acid | 71-73% |
| Nitric acid | 0.2-0.8% |
| Nitrous acid | 0.3-0.7% |
| Dinitrotoluene | 0.2-0.4% |
| Mononitrotoluene | 0.1-0.3% |
| Nitrocresols | 20-50 ppm |

| -continued | |
|---|---|
| Water | Balance |

A 1000 gram portion of spent acid was contacted with a 50 g portion of toluene and a dark reddish brown color appeared in the acid layer and remained through conventional concentration.

EXAMPLE 2

The spent acid in Example 1 was utilized except that the $HNO_2$ composition was 0.74% and refined in accordance with the process of this invention. Several 100 gram samples of acid were treated with various oxidizing and reducing agents in a stirred tank at a temperature of 0° and 25° C. at various mole ratios to determine their effectiveness for removing nitrous acid. Table 1 below represents these results.

TABLE 1

| Oxidizer/Reducer | Mole/Mole $HNO_2$ | Temp °C. | Reaction Time Min | % $HNO_2$ Remaining | Oxidation/Reduction Efficiency |
|---|---|---|---|---|---|
| $H_2O_2$ | 0.2 | 25 | 5–10 | 0.68 | 0.41 |
| $H_2O_2$ | 1.0 | 25 | 5–10 | 0.19 | 0.74 |
| $H_2O_2$ | 1.2 | 0 | 5–10 | 0.08 | 0.74 |
| $H_2O_2$ | 1.6 | 25 | 5–10 | 0.00 | — |
| Ammonium persulfate | 0.8 | 25 | 5–10 | 0.18 | 0.95 |
| Ammonium persulfate | 1.2 | 25 | 5–10 | 0.00 | — |
| Potassium persulfate | 0.8 | 0 | 5–10 | 0.36 | 0.64 |
| Potassium persulfate | 1.2 | 25 | 5–10 | 0.00 | — |
| Air sparge | | 25 | 17 min. | 0.67 | — |
| Air sparge | | 25 | 1658 min. | 0.28 | — |
| Sodium chlorate | 0.5 | 25 | 5–10 | 0.38 | 0.97 |
| Sodium chlorate | 1.0 | 25 | 5–10 | 0.07 | 0.91 |
| Sodium chlorate | 1.5 | 25 | 5–10 | 0.0 | — |
| Sulfamic acid | 1.0 | 25 | 5–10 | 0.02 | 0.97 |
| Sulfamic acid | 1.0 | 45 | 5–10 | 0.04 | 0.64 |
| urea | 0.5 | 25 | 10.2 | 0.54 | 0.54 |
| urea | 0.5 | 25 | 4 hours | 0.36 | 1.00 |

The above results show that a variety of oxidizing and reducing agents are effective for removing $HNO_2$ from the spent acid in the nitration of toluene. $H_2O_2$ at a 1.6:1 mole ratio results in a slight pink color. Thus, oxidizer levels above 1.5:1 moles/mole $HNO_2$ generally should be avoided not only because of cost, but because of color generation. Sulfamic acid is the preferred reagent because of its low cost and because the by products of the reaction are non-contaminating to the system. However, it takes substantial time to dissolve. Hydrogen peroxide although non-contaminating is costly.

EXAMPLE 3

Spent acids in Example 1 were used and refined in five vessels in series in accordance with the process of this invention. According to Example 2, spent acids were treated in two stirred vessels (Vessel 1 and 2). A 1.1 mole equivalent of $H_2O_2$ was present in the first vessel with urea being used in the second vessel. Toluene in various volume ratios to that of spent acid was passed through Vessel 3 and 4 for denitrification. Extracted spent acid and toluene extract were separated in Vessel 5. The spent acid from each vessel was analyzed to determine nitric acid concentration to monitor the efficiency of the described process. Dashes in columns 4 & 5 indicate the concentration of $HNO_3$ was nil.

| | Residence time each vessel (MIN) | | | | | Phase Ratio |
|---|---|---|---|---|---|---|
| Run | 1 | 2 | 3 | 4 | 5 | Toluene/$H_2SO_4$ |
| 1 | 12 | 12 | 9.3 | 9.3 | 2.5 | 1/3 |
| 2 | 12 | 12 | 7.4 | 7.4 | 2.0 | 2/3 |
| 3 | 12 | 12 | 6.2 | 6.2 | 1.7 | 1/1 |

| | | $HNO_3$ Concentration PPM Vessel | | | | |
|---|---|---|---|---|---|---|
| Run | Temp | 1 | 2 | 3 | 4 | 5 |
| 1 | 25° C. | — | 3440 | 287 | — | — |
| 2 | 25° C. | 2026 | 1644 | 1 | — | — |
| 3 | 25° C. | 7264 | 7264 | 2465 | — | — |

It was noted that the spent acid phase in vessles 3, 4 and 5 became slightly discolored as toluene was continuously passed through the stage. This reddish cast was believed due to the formation of nitrous acid formed by the reaction of $HNO_3$ with the toluene during scrubbing and the subsequent reaction of the $HNO_2$ with toluene. This reddish color was eliminated from the acid in vessel 3 by inroducing small amounts, e.g. 0.1–0.2% by weight of urea (Run 3) and sulfomic acid (Runs 1 and 2). Spent acid from the other vessels was clear. This test shows that the oxidizing of the spent acid to remove $HNO_2$ preferably to a level below about 1 ppm prior to scrubbing with toluene will result in reduced color formation.

EXAMPLE 4

The spent acid from run 3 in Example 3 is combined with a 5% by weight aqueous solution of hydrogen peroxide mixture, the hydrogen peroxide being present in an amount to provide 1.6 equivalents of hydrogen peroxide per equivalent of nitrocresol. The acid-$H_2O_2$ combination is heated to a temperature of 145° C. for a period of one-half hour. On analysis, the total amount of organic impurities remaining in the spent sulfuric acid is about 27 parts per million. The $HNO_3$ and $HNO_2$ content were negligible. The resulting acid then was ready for concentration or sale in dilute form.

What is claimed is:

1. In a process for the manufacture of a nirotoluene compound by reacting toluene with an aqueous acid mixture comprising nitric acid and sulfuric acid under conditions sufficient to effect nitration thereof and form a nitrotoluene compound and a spent aqueous acid fraction and then recovering the nitrotoluene compound from the spent aqueous acid fraction, the improvement for refining the spent aqueous acid fraction which comprises the following steps:
  (a) contacting said spent aqueous acid with at least a stoichiometric quantity of an oxidizing or reducing agent under conditions effective for destroying contaminant nitrous acid contained therein; and
  (b) contacting the spent aqueous acid substantially free of nitrous acid in step (a) with a sufficient quantity of feed toluene to remove residual nitric acid leaving a mixture consisting essentially of sulfuric acid and contaminant organic impurities.

2. The process of claim 1 wherein a reducing agent is used in step (a) and the reducing agent is sulfamic acid.

3. The process of claim 1 wherein in step (a) the oxidizing agent is selected from the group consisting of hydrogen peroxide, peroxydisulfates, chlorates, and mixtures thereof.

4. The process of claim 3 wherein the oxidizing agent is present at a level from stoichiometric to 1.6 moles per mole of $HNO_2$ in step (a).

5. The process of claim 4 or 2 wherein the quantity of feed toluene utilized to extract residual nitric acid is at a lvel of from about 10–100% by volume of the total feed toluene being nitrated.

6. The process of claim 5 wherein if said contaminant organic impurities in step (b) are present in a proportion greater than 100 ppm, then step (b) is followed by step (c) wherein the aqueous acid mixture from step (b) is contacted with an oxidizing agent under conditions for effecting oxidation of said contaminant organic impurities to a level below about 50 ppm.

7. The process of claim 6 wherein the oxidizing agent used to remove said contaminant organic impurities in step (c) is selected from the group consisting of ozone, hydrogen peroxide, peroxydisulfates, chlorates and mixtures thereof.

8. The process of claim 7 wherein the nitrotoluene compound is dinitrotoluene.

* * * * *

UNITED STATES PATENT AND TRADEMARK OFFICE
CERTIFICATE OF CORRECTION

PATENT NO. : 4,257,986
DATED : 24 March 1981
INVENTOR(S) : Barton Milligan, Der-Shing Huang It is certified that error appears in the above-identified patent and that said Letters Patent are hereby corrected as shown below:

Column 1, Line 61
    Delete "agueous" and substitute therefor
    --aqueous--

Column 2, Line 49
    Delete "curde" and substitute therefor
    --crude--

Column 4, Line 44
    Delete "iss" and substitute therefor --is--

Column 6, Line 17
    Delete "vessles" and substitute therefor
    --vessels--

Column 6, Line 24
    Delete "inroducing" and substitute therefor
    --introducing--

Column 7, Line 6
    Delete "lvel" and substitute therefor
    --level--

Signed and Sealed this

Eighth Day of September 1981

[SEAL]

Attest:

GERALD J. MOSSINGHOFF

Attesting Officer     Commissioner of Patents and Trademarks